United States Patent [19]

Staab et al.

[11] Patent Number: 4,999,441
[45] Date of Patent: Mar. 12, 1991

[54] TETRAKIS(DIALKYLAMINO)AROMATICS AND THEIR CHARGE TRANSFER COMPLEXES

[75] Inventors: Heinz A. Staab, Heidelberg; Karin Elbl, Neckarsulm, both of Fed. Rep. of Germany

[73] Assignee: Max-Planck-Gesellschaft zur Foerderung der Wissenschaften e.V., Goettingen, Fed. Rep. of Germany

[21] Appl. No.: 339,868

[22] Filed: Apr. 17, 1989

Related U.S. Application Data

[63] Continuation of Ser. No. 97,112, Sep. 16, 1987, abandoned.

[30] Foreign Application Priority Data

Sep. 17, 1986 [DE] Fed. Rep. of Germany ....... 3631614

[51] Int. Cl.$^5$ ................. C07C 225/24; C07C 255/31; C07C 255/58
[52] U.S. Cl. .................................. 552/291; 552/301; 552/303; 552/308; 556/76; 558/403; 558/419; 562/84; 562/480; 562/493; 562/607; 564/290; 564/307; 564/308; 564/427; 564/428
[58] Field of Search .................. 260/396 N; 564/436, 564/308, 307, 290, 305, 427, 428, 305, 427, 428; 552/303, 291, 308, 301; 556/76; 562/607, 493, 84, 480; 558/419, 403

[56] References Cited

U.S. PATENT DOCUMENTS 2,938,004  5/1960  De Hoff et al. ................. 564/307
3,162,641 12/1964  Acker et al. ..................... 260/396 N

FOREIGN PATENT DOCUMENTS 3335589  4/1985  Fed. Rep. of Germany ... 260/396 N

OTHER PUBLICATIONS

Borch et al., (1972), J. Org. Chem., 37(10):1637-1674.
Ber., vol. 12 (1879), paper 522-528.
Ber., vol. 12 (1879), paper 2071-2072.
Ber., vol. 20 (1887), paper 328-338.
Ber., vol. 25 (1892), paper 2826-2846.
Angew. Chemie, vol. 98 (1986) paper 460-461.
Karin Elbl et al., Angewandte Chemie, International Edition, vol. 25, No. 11, Nov. 1986, pp. 1023-1024.

Primary Examiner—Vivian Garner
Attorney, Agent, or Firm—Keil & Weinkauf

[57] ABSTRACT

Tetrakis(dialkylamino)aromatics Ia to Ic

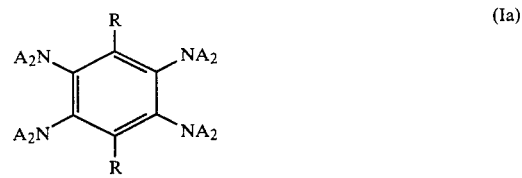

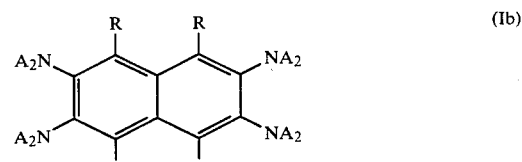

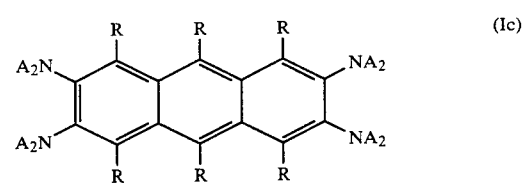

where the radicals A may be identical or different and are n-$C_1$-$C_6$-alkyl and the radicals R may be identical or different and are hydrogen or $C_1$-$C_6$-alkyl, and their charge transfer complexes with electron acceptors, and the preparation of Ia to Ic from the corresponding N-unsubstituted amines by alkylation with A'—CHO (where A'=H or N-$C_1$-$C_5$-alkyl) and reduction with NaBH$_3$CN.

The charge transfer complexes of Ia and Ic are used to prepare electrically conductive polymers.

4 Claims, No Drawings

TETRAKIS(DIALKYLAMINO)AROMATICS AND THEIR CHARGE TRANSFER COMPLEXES

This application is a continuation of application Ser. No. 097,112, filed on Step. 16, 1987, now abandoned.

The invention relates to tetrakis(dialkylamino)-aromatics, their charge transfer complexes, a process for the preparation of these compounds and the use of the complexes for the preparation of conductive polymers.

Ber. Dt. Chem. Ges. 12 (1879) 522, 2071 describes 1,4-bis(dimethylamino)benzene, also referred to as N,N,N'N'-tetramethyl-para-phenylenediamine. Because of its high donor strength, this compound is one of the most extensively investigated electron donors in organic chemistry.

1,2-bis(Dimethylamino)benzene was described in Ber. Dt. Chem. Ges. 25 (1892) 2826. 1,2,4,5-Tetraaminobenzene is also known, cf. Ber. Dt. Chem. Ges. 20 (1887), 328. Finally, Angew. Chem. 98 (1986), 460, describes investigations of compounds with spatially adjacent dimethylamino groups which act as proton sponges.

It is an object of the present invention to provide novel tetrakis(dialkylamino)aromatics which exhibit interesting properties and are in particular suitable for forming conductive charge transfer complexes.

We have found that this object is achieved by providing novel tetrakis(dialkylamino)aromatics of the general formulae Ia to Ic

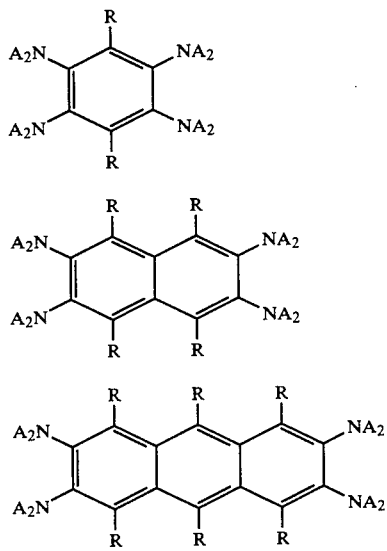

where the radicals A may be identical or different and are n-$C_1$-$C_6$-alkyl and the radicals R may be identical or different and are hydrogen or $C_1$-$C_6$-alkyl, and their charge transfer complexes with electron acceptors.

Among these compounds, those of formula Ia where A is n-$C_1$-$C_4$-alkyl and R is hydrogen or $C_1$-$C_4$-alkyl are preferred, 1,2,4,5-tetrakis(dimethylamino)benzene being the compound of greatest importance.

The invention also relates to a process for the preparation of tetrakis(dialkylamino)aromatics Ia to Ic and of their charge transfer complexes, wherein the corresponding N-unsubstituted tetramines IIa to IIc

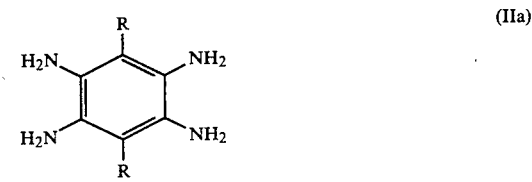

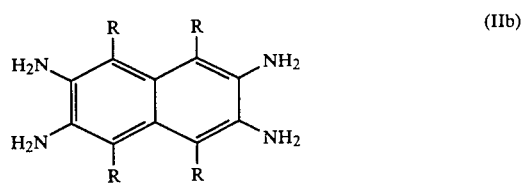

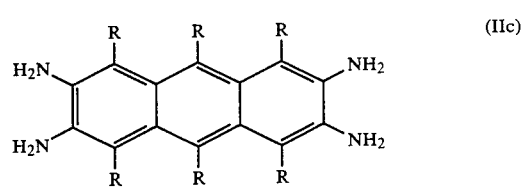

or their acid addition salts are reacted, in a water-soluble polar solvent and in the presence of sodium cyanoborohydride $$NaBH_3CN$$

with an aldehyde of the general formula III

where A' is hydrogen or n-$C_1$-$C_5$-alkyl, and, if desired, the product obtained is reacted with an electron acceptor to form a corresponding charge transfer complex.

According to a preferred embodiment of the process according to the invention, the method of which is known per se from J. Org. Chem. 37 (1972), 1673, the tetramines IIa to IIc are reacted with aqueous formaldehyde, of concentration advantageously from 30 to 40, more especially from 35 to 38, % by weight, to give the N-permethylated compounds Ia to Ic.

To prepare the charge transfer complexes of the compounds Ia to Ic, the particular tetrakis(dialkylamino)-aromatic, dissolved or suspended in an inert solvent, can be reacted with the appropriate electron acceptor in a conventional manner.

If the electron acceptor corresponds to an anion, preferably halide, triiodide, nitrate, perchlorate, tetrafluoborate, hexafluorophosphate, hexafluoroarsenate or the anion of an organic $C_1$-$C_{12}$ acid, for example acetic acid, benzoic acid, terephthalic acid or p-toluenesulfonic acid, the complex is advantageously prepared electrochemically by subjecting an organic solution of the donor (I)-(BASF) acetonitrile is frequently a very suitable solvent-and of a metal salt or ammonium salt, for example silver nitrate, to electrolysis. Hereupon, the cation is discharged at the cathode while at the anode the transfer complex with up to two charges per molecule I, for example I++ (NO$_3$)$_2^-$, is formed.

One of the possible limiting structures of the donor cation can be written as follows

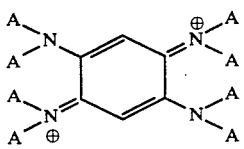

but in actual fact the position of the charge cannot be localized, because there is complete mesomerism.

Once one of these cation-anion complexes has been obtained, the anion can be replaced by another anion, for example by means of an anion exchanger.

Amongst the anions, the anion pair iodide/triiodide, formed by reaction of (I) with iodine, is of particular importance.

Originally nonanionic acceptors, i.e. τ-electron acceptors (which, for example, also include iodine) are generally of major interest, because of the conductivity properties of the complexes. Examples of such compounds are tetracyano-p-quinodimethane, tetrachloro-o-benzoquinone, dicyanodichloro-p-benzoquinone, tetracyanoethylene, nitroarines and tetracyanobenzene, i.e. compounds in general which because of their substituents and structural units (halogen, nitro groups, cyano groups, aromatic or conjugated systems) exhibit high electron affinity.

Preparation of these complexes is in general particularly simple, since they are formed upon bringing the components together and in most cases constitute precipitates which then need only be filtered off.

Since the conductivity of the complexes increases with purity, it is advisable to employ the components, i.e. the donor and acceptor, in a very pure form. Suitable purification methods are crystallization and distillation; tetrakis(dimethylamino)benzene can also be purified by sublimation.

It is advisable to carry out the process under an inert gas, since the compounds according to the invention, present in solution or suspension, are readily oxidized by oxidants such as atmospheric oxygen, giving a green coloration.

The solvents used in the preparation of the compounds according to the invention are polar water-miscible solvents, especially acetonitrile. However, other solvents, for example propionitrile, dimethylsulfoxide and dimethylformamide, may also be used.

Most of the charge transfer complexes according to the invention are of great interest for numerous applications, because of their conductivity. They are used, in particular, for the preparation of conductive polymers, the production of organic batteries and the antistatic treatment of polymers. Furthermore they can, because of their semiconductor properties, be used in electronics.

Plastics into which the charge transfer complexes according to the invention can be incorporated include a great variety of polymers, for example polyolefins, e.g. polyethylene, homopolymers and copolymers of styrene, α-methylstyrene, p-methylstyrene, butadiene, acrylonitrile, methacrylonitrile, acrylates and methacrylates, polyisoprene, polyesters, e.g. polyethyleneterephthalate, polypyrroles, nylons, e.g. nylon-6,6, polycarbonates, polysulfones, homopolymers and copolymers which contain vinyl acetate, vinylcarbazole, vinyl chloride, vinylpyridine, vinylpyrrolidone**, vinylidene chloride, vinylidene fluoride, olefins, acrylic acid, acrylic esters, acrylamide, methacrylic acid, methacrylic esters, methacrylamide, maleic acid and maleic esters, and/or which have recurring linking units, such as urethane, carbonate, ester, amide, ether, thioether, acetal, ketone or sulfone groups, in their main chain.

Conductivity measurements on a typical charge transfer complex according to the invention, namely on the 1:2 complex (2 molecules of TCNQ per molecule of donor) of 1,2,4,5-tetrakis(dimethylamino)benzene with tetracyanoquinodimethane (TCNQ) gave a conductivity (single crystal, four contact method) for this complex of $\sigma \sim 10^{-1}(\Omega cm)^{-1}$. The temperature dependence of the conductivity shows that one is dealing with a typical semiconductor.

EXAMPLE 1

Preparation of 1,2,4,5-tetrakis(dimethylamino)benzene 568 mg (2 mmol) of 1,2,4,5-tetraaminobenzene tetrahydrochloride were suspended in 30 ml of acetonitrile under an inert gas. 3 ml of 36.5% formaldehyde solution (39.7 mmol) and 700 mg (11.1 mmol) of sodium cyanoborohydride were added to the mixture. After 15 minutes, the batch was neutralized with a few drops of glacial acetic acid.

The mixture was stirred for 3 hours and the solvent was then distilled off under reduced pressure from a water pump. The residue was taken up in 40 ml of aqueous 2 N potassium hydroxide solution and extracted with ether until the organic phase was colorless. The combined organic extracts were washed with 30 ml of 0.5 N KOH solution. They were then extracted by shaking with three 20 ml portions of 1 N hydrochloric acid. Solid KOH was then added to the acid phase until the solution turned cloudy and showed an alkaline reaction. It was then again extracted with ether, the extract was dried over potassium carbonate and the solvent was evaporated off. The residue was sublimed twice at 4–5.3 mbar and 90°–100° C. oil bath temperature. 135 mg (27% of theory) of colorless crystals, of melting point 95° C., were obtained.

1H NMR spectrum (360 MHz, CDCl$_3$): $\delta=6.56$ (s, 2H, Ar—H), $\delta=2.76$ (s, 24H, N-CH$_3$)

Mass spectrum (T$_Q$=90°–100° C.): m/z (I%) 250 (100; M+), 235 (6), 220 (12), 125 (3; M++)

IR spectrum (KBr): 2980, 2940, 2820, 2790, 1510 cm$^{-1}$

UV spectrum (CH$_3$CN): $\lambda_{max}$ (log ε) 242 (4.32), 278 (3.85), 320 (3.68) nm

EXAMPLE 2

Preparation of the 1,2,4,5-tetrakis(dimethylamino)benzene dication iodide-triiodide 25 mg (0.1 mmol) of 1,2,4,5-tetrakis(dimethylamino)benzene were dissolved in a small amount of acetonitrile and a solution of 50.8 mg (0.2 mmol) of iodine in acetonitrile was added. Blackish violet crystals having a metallic luster separated out from the dark green solution. They were recrystallized from acetonitrile.

Yield: 29.2 mg (38.5% of theory), melting point 272° C. (with evolution of iodine from 195° C. onward). The empirical formula corresponds to the above composition of a dicationiodide-triiodide complex.

$^1$H NMR spectrum (360 MHz, [D$_6$]DMSO): $\delta=5.85$ (s, 2H) $\delta=3.34$ (s, 24H, N-H$_3$)

IR spectrum (KBr): 1563, 1405, 1330, 1157 cm$^{-1}$

UV spectrum (CH₃CN): λmax (log ε) 290 (4.74), 368 (4.46), 392 sh (4.43), 5.73 (3.38) nm

EXAMPLE 3

Preparation of a complex of 1,2,4,5-tetrakis(dimethylamino)benzene with tetracyanoquinodimethane (TCNQ)

25 mg (0.1 mmol) of 1,2,4,5-tetrakis(dimethylamino)benzene were dissolved in acetonitrile and a solution of 41 mg (0.2 mmol) of TCNQ in acetonitrile was added. The dark green solution was heated to 80° C. On cooling to room temperature, violet glossy needles formed. Yield: 29.1 mg (44.2% of theory); melting point: 213° C. (with decomposition). The empirical formula corresponds to the 1:2 donor-acceptor complex.

IR spectrum (KBr): 2160 (C≡N), 1555, 1325, 1125, 953, 825, 690 cm⁻¹

UV spectrum (CH₃CN): λmax (log ε) 392 (5.29), 676 (3.90), 40 (4.39), 836 (4.61) nm

We claim:
1. A charge transfer complex comprising an electron donor of the formula Ia, Ib or Ic

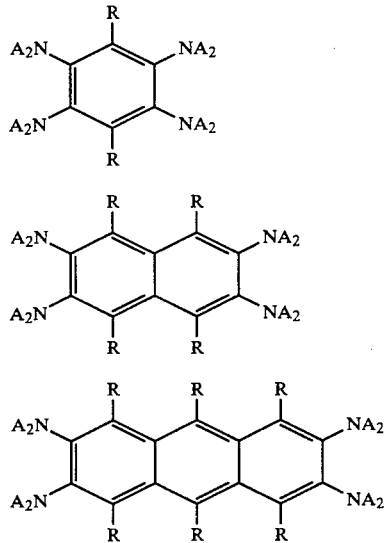

where the radicals A may be identical or different and are n-C₁-C₆-alkyl and the radicals R may be identical or different and are hydrogen or C₁-C₆-alkyl, and an electron acceptor selected from an anion selected from the group consisting of halides, nitrate, perchlorate, tetrafluoroborate, hexafluorophosphate, hexafluoroarsenate or an anioin of acetic acid, benzoic acid, terephthalic acid or p-toluensulfonic acid or a compound selected from the group consisting of tetracyano-p-quinodimethane, tetrachloro-o-benzoquinone, dicyanodichloro-p-benzoquinone, tetracyanoethylene or tetracyanobenzene.

2. A tetrakis(dialkylamino) aromatic of the formula Ia, Ib or Ic

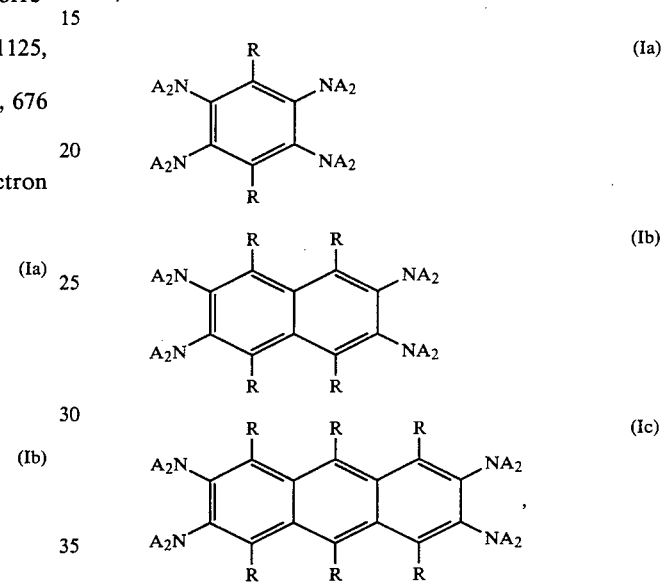

where the radicals A may be identical or different and are n-C₁-C₆-alkyl and the radicals R may be identical or different and are hydrogen or C₁-C₆-alkyl.

3. A 1,2,4,5-tetrakis(dialkylamino)benzene of the formula Ia, as defined in claim 2, where A is n-C₁-C₄-alkyl and R is hydrogen or C₁-C₄-alkyl.

4. 1,2,4,5-tetrakis(dimethylamino)benzene.

* * * * *